| United States Patent [19] | [11] Patent Number: 4,804,743 |
| Kaltenbronn et al. | [45] Date of Patent: Feb. 14, 1989 |

[54] PROLINE-CONTAINING RENIN INHIBITORS

[75] Inventors: James S. Kaltenbronn; Elizabeth A. Lunney, both of Ann Arbor, Mich.; Ernest D. Nicolaides, Ramona, Calif.

[73] Assignee: Warner-Lambert Copmany, Morris Plains, N.J.

[21] Appl. No.: 8,702

[22] Filed: Jan. 29, 1987

[51] Int. Cl.$^4$ .......................... C07K 7/06; C07K 5/10; A61K 37/02

[52] U.S. Cl. .................................... 530/330; 530/331; 530/338

[58] Field of Search ................. 530/330, 331; 514/15, 514/16, 17

[56] References Cited

U.S. PATENT DOCUMENTS

| 4,191,753 | 3/1980 | Ryan | 514/15 |
| 4,384,994 | 5/1983 | Veber et al. | 530/330 |
| 4,479,941 | 10/1984 | Veber | 514/17 |
| 4,481,192 | 11/1984 | Cazaubon et al. | 530/330 |
| 4,595,677 | 6/1986 | Riniker et al. | 530/330 |
| 4,629,724 | 12/1986 | Ryono et al. | 530/330 |
| 4,663,310 | 5/1987 | Bock et al. | 530/330 |
| 4,668,769 | 5/1987 | Hoover | 530/330 |
| 4,749,687 | 6/1988 | Bindra | 514/18 |

FOREIGN PATENT DOCUMENTS

85/308759 7/1986 European Pat. Off. .
84/03044 8/1984 PCT Int'l Appl. .

*Primary Examiner*—Delbert R. Phillips
*Assistant Examiner*—T. D. Wessendorf
*Attorney, Agent, or Firm*—Elizabeth M. Anderson

[57] ABSTRACT

This invention concerns novel renin-inhibitory peptides containing proline which are useful for treating renin associated hypertension and for treating hyperaldosteronism. Intermediates and processes for preparing both the intermediates and the novel peptides, pharmaceutical compositions, and methods of treatment are included. Also included is a method of diagnosis of renin-associated hypertension using the compounds of the invention.

5 Claims, No Drawings

PROLINE-CONTAINING RENIN INHIBITORS

BACKGROUND OF THE INVENTION

Renin is a natural enzyme which is released into the blood from the kidney. It cleaves its natural substrate, angiotensinogen, releasing a decapeptide, angiotensin I. This is in turn cleaved by converting enzyme in the lung, kidney and other tissues to an octapeptide, angiotensin II. Angiotensin II raises blood pressure both directly by causing arteriolar constriction and indirectly by stimulating release of the sodium-retaining hormone aldosterone from the adrenal gland causing a rise in extracellular fluid volume. Inhibitors of renins have been sought as an agent for control of hypertension and hyperaldosteronism.

U.S. Pat. No. 4,479,941 covers certain renin-inhibitory peptides of the formula

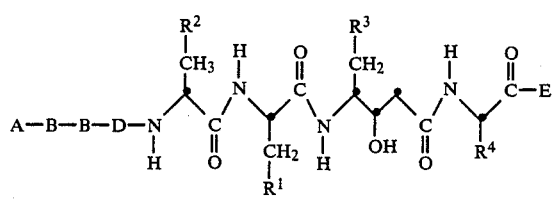

European Application No. 85308759 covers certain renin-inhibitory dipeptides of the formula

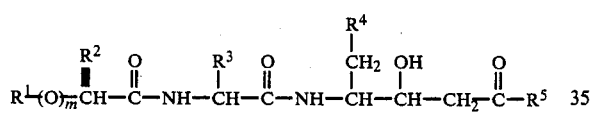

wherein m is 0 or 1 and $R^1$–$R^5$ are a variety of organic groups

The present invention concerns novel proline-containing peptides which inhibit renin. The present invention is also concered with pharmaceutical compositions containing the novel peptides, methods of treating renin-associated hypertension and of treating hyperaldosteronism, and methods for preparing the novel peptides.

SUMMARY

The present invention relates to novel peptides of the formula

ACYL—X—Y—T—U—V—W    I and the pharmaceutically acceptable acid addition salts thereof wherein ACYL, X, Y, T, U, V, and W are defined herein below.

The present invention further includes a process for preparing compounds of Formula I above. The present invention also includes a pharmaceutical composition comprising an effective amount of a peptide of Formula I in admixture with a pharmaceutically acceptable carrier or excipient and a method for treating renin-associated hypertension in a patient suffering therefrom comprising administering to said patient the above pharmaceutical composition in unit dosage form.

Further the present invention includes a pharmaceutical composition comprising an effective amount of a peptide of Formula I in admixture with a pharmaceutically acceptable carrier or excipient and a method for treating hyperaldosteronism in a patient suffering therefrom comprising administering to said patient the above pharmaceutical composition in unit dosage form.

Also included in a method for determining the presence of renin-associated hypertension in a patient.

DETAILED DESCRIPTION

The following table provides a dictionary of the terms used in the description of the present invention.

TABLE I

| Abbreviated Designation | Name |
|---|---|
| Protecting and Other Acyl Groups | |
| BOC | Tert-butyloxycarbonyl |
| IBU | Isobutyryl |
| IVA | Isovaleryl |
| NVA | n-Valeryl |
| Z | Benzyloxycarbonyl |
| DNMA | Di-(α-naphthylmethyl)-acetyl |
| TRT | Trityl |
| AMIDES | |
| —NHCH$_2$Ph | Benzylamine |
| —NHCH$_2$— 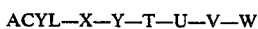 | Cyclohexylmethylamine |
| —NHCH$_2$—(C$_6$H$_4$)—CH$_2$NHZ (BOC) | m-Xylylenediamine (Z or BOC) |
| —NHCH$_2$—(C$_6$H$_4$)—CH$_2$NH$_2$ | m-Xylylenediamine |
| —NH—(piperidine)—N—CH$_2$Ph | 4-Amino-N—benzyl-piperidine |
| —NH—(piperidine)—NH | 4-Aminopiperidine |
| —NHCH$_2$—(pyridine) | 2-Aminomethylpyridine |
| —NHCHCH(CH$_3$)CH$_2$CH$_3$ <br> CH$_2$OH | 1-hydroxymethyl-2-methyl-butylamine |
| —NHCH$_2$CH(CH$_3$)CH$_2$CH$_3$ | 2-Methylbutylamine |
| —NH—CH$_2$CH$_2$—N(morpholine)O | 4-aminoethylmorpholine |
| AMINO ACIDS | |
| PHE | L—Phenylalanine |
| LEU | L—Leucine |
| STA | Statine |
| MET | L—Methionine |
| PRO | L—Proline |
| MET(O) | L—Methionine sulfoxide |

TABLE I-continued

| Abbreviated Designation | Name |
|---|---|
| GLU | L—Glutamic acid |
| GLU(OCH₂Ph) | L—Glutamic acid, γ-benzyl ester |
| GLN | L—Glutamine |
| GLY | Glycine |
| NLE | L—Norleucine |
| MET(O)₂ | L—Methionine sulfone |
| ILE | L—Isoleucine |
| VAL | L—Valine |
| HIS | L—Histidine |
| HOMOPHE | L—Homophenylalanine |
| NAPHTHYLALA | L—(1-Naphthyl)alanine |
| PHSTA | 4(S)—Amino-3(S)—hydroxy-5-phenylpentanoic acid |
| CYSTA | 4(S)—Amino-3(S)—hydroxy-5-cyclohexanepentanoic acid |
| TRP | L—Tryptophane |
| CYCLOHEXYLALA | Cyclohexylalanine |
| ARG | L—Arginine |
| ARG(NO₂) | L—Nitroarginine |
| GLU(OCH₃) | L—Glutamic acid, γ-methyl ester |
| GLU(OC₂H₅) | L—Glutamic acid, γ-ethyl ester |
| SMeCYS | L—S—Methylcysteine |
| SOMeCYS | L—S—Methylcysteine sulfoxide |
| (Me⁵)PHE | Pentamethylphenylalanine |
| CYS | L—Cysteine |
| ASP | L—Aspartic Acid |
| ASP(OCH₃) | L—Aspartic acid, β-methyl ester |
| ASP (OC₂H₅) | L—Aspartic acid, β-ethyl ester |
| ASP(OCH₂Ph) | L—Aspartic acid, β-benzyl ester |
| ASP(O—t-Bu) | L—Aspartic acid, β-t-butyl ester |
| ASN | L—Asparagine |
| SER | L—Serine |
| SER(CH₂Ph) | L—Serine, O—benzyl ether |
| SER(CH₃) | L—Serine, O—methyl ether |
| SER(C₂H₅) | L—Serine, O—ethyl ether |
| ALA | L—Alanine |
| ORN | L—Ornithine |
| ORN(Z) | L—Ornithine, δ-Z |
| ORN(BOC) | L—Ornithine, δ-BOC |
| ORN(PHT) | L—Ornithine, δ-phthaloyl |
| ORN(Ac) | L—Ornithine, δ-acetyl |
| Lys | L—Lysine |
| Lys(Z) | L—Lysine, ε-Z |
| Lys(BOC) | L—Lysine, ε-BOC |
| Lys(PHT) | L—Lysine, ε-phthaloyl |
| Lys(Ac) | L—Lysine, ε-acetyl |
| GLU(O—t-Bu) | L—Glutamic acid, γ-t-butyl ester |
| HYDROXYPRO | L—Hydroxyproline |
| ESTERS | |
| OCH₃ | Methanol |
| OC₂H₅ | Ethanol |
| REAGENTS | |
| DCC | N,N'—dicyclohexylcarbodiimide |
| HOBT | Hydroxybenzotriazole |
| TFA | Trifluoroacetic acid |
| DMF | N,N—Dimethylformamide |

The peptide of the present invention are represented by the formula

ACYL—X—Y—T—U—V—W    I or a pharmaceutically acceptable salt thereof, wherein
ACYL is BOC, IBU, IVA, NVA, Z, or DNMA;

X is absent, PHE, HOMOPHE, NAPHTHYLALA, TRP, CYCLOHEXYLALA, (Me⁵)PHE, VAL, ILE or LEU, with the proviso that when X is absent ACYL is DNMA;

Y is CYS, SMeCYS, SOMeCYS, SO₂MeCYS, ASP, ASP(OCH₃), ASP(OC₂H₅), ASP(OCH₂Ph), ASP-(O-t-Bu), ASN, SER, SER(CH₂Ph), SER(CH₃), SER(C₂H₅), LEU, GLY, ILE, VAL, NLE, HIS, PHE, ARG, ARG(NO₂), ALA, ORN, ORN(Z), ORN(BOC), ORN(PHT), ORN(Ac), LYS, LYS(Z), LYS(BOC), LYS(PHT), LYS(Ac), GLN, GLU, GLU(OCH₂Ph), GLU(O-t-Bu), GLU(OCH₃), GLU(OC₂H₅), MET, MET(O), MET(O)₂,

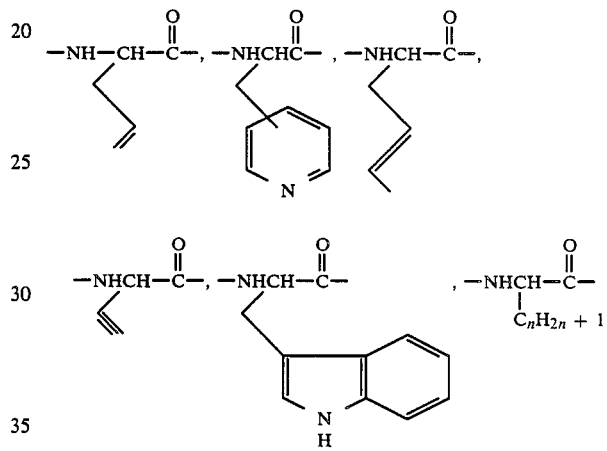

wherein n is an integer of 2, or 4–10,

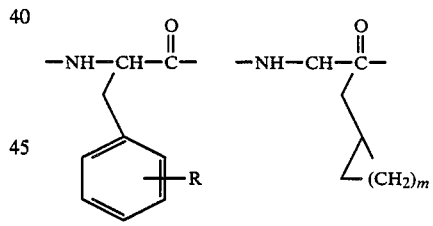

wherein R is alkyl, halogen or alkoxy,    wherein m is an integer, of from 1 to 3

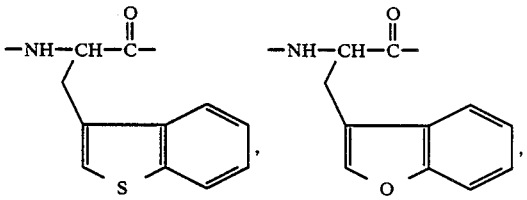

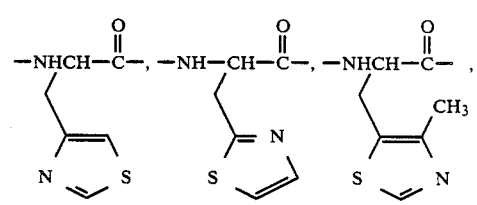

-continued

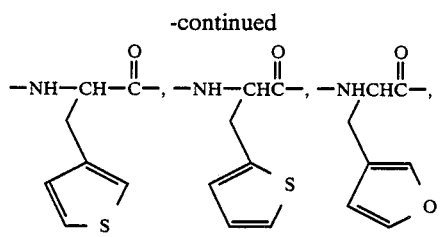

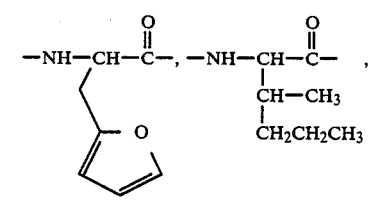

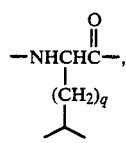

wherein q is an integer of from 2 to 4,

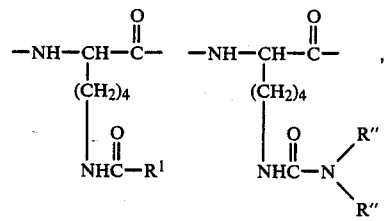

where $R^1$ is an alkyl group of from 1–4 carbon atoms,

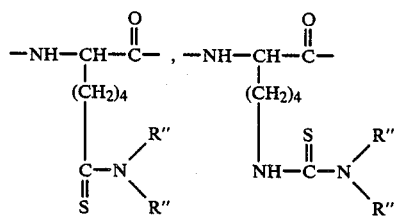

wherein R" is H or an alkyl of from 1 to 4 carbon atoms;

T is STA, PHSTA, OR CYSTA;
U is absent, GLU, GLU(OCH$_2$Ph), GLU(OCH$_3$), GLN, MET, MET(O), SMeCYS, GLU(OC$_2$H$_5$), GLU(O-t-Bu), SOMeCYS, ASP, ASP(OCH$_2$Ph), ASP(OCH$_3$), ASP(OC$_2$H$_5$), ASN, 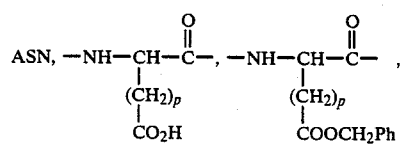

-continued

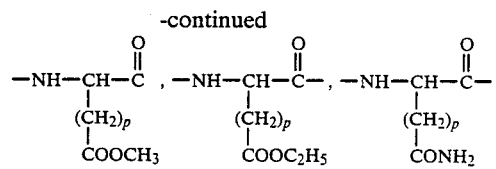

wherein p is the integer 3 or 4;
V is PRO, HYDROXYPRO, piperidine-2-carboxylic acid,

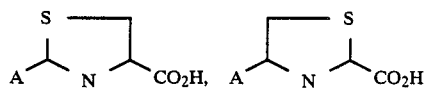

wherein A is an alkyl of from one to four carbon atoms, aralkyl, or aryl wherein aryl is a single ring such as phenyl optionally substituted with a lower alkyl or halogen, and other similar secondary amines, and
W is

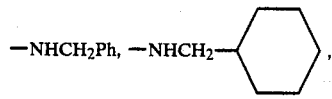

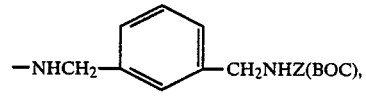

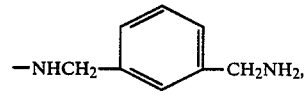

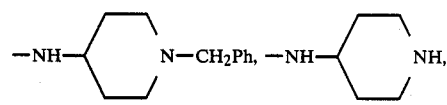

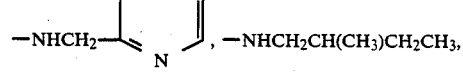

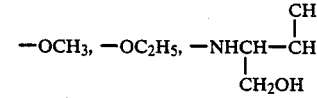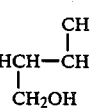

Preferred compounds of the present invention are according to Formula I above wherein
ACYL is BOC, IBU, IVA, NVA, Z, or DNMA;
X is absent, PHE, HOMOPHE, NAPHTHYLALA, TRP, or CYCLOHEXYLALA; with the proviso that when X is absent, ACYL is DNMA;
Y is LEU, GLY, ILE, VAL, NLE, HIS, PHE, ARG, or ARG(NO$_2$);
T is STA, PHSTA, or CYSTA;

U is absent, GLU, GLU(OCH₂Ph), GLU(OCH₃), MET(O)₂, GLN, MET, MET(O), SMeCYS, GLU(OC₂H₅), or SOMeCYS;
V is PRO; and
W is

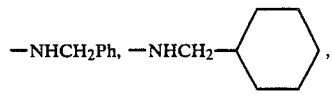

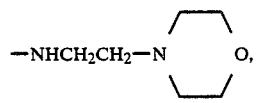

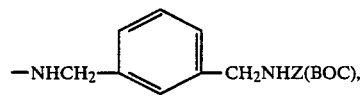

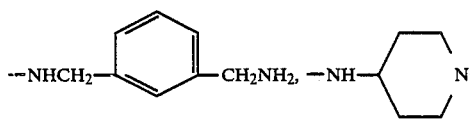

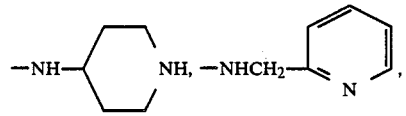

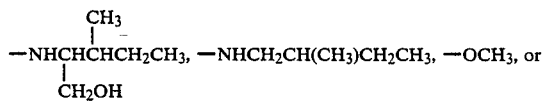

—OC₂H₅.

Particularly valuable compounds falling within the scope of the invention include the following compounds:
BOC-PHE-LEU-STA-MET-PRO-NHCH₂Ph,
BOC-PHE-LEU-STA-MET(O)-PRO-NHCH₂Ph, DNMA-LEU-STA-MET-PRO-NHCH₂Ph,
DNMA-LEU-STA-MET(O)-PRO-NHCH₂Ph, BOC-PHE-LEU-STA-PRO-NHCH₂Ph,
BOC-PHE-LEU-STA-GLU(OCH₂Ph)-PRO-OCH₃,
BOC-PHE-GLY-STA-GLU(OCH₂Ph)-PRO-OCH₃, and
BOC-PHE-LEU-STA-GLN-PRO-OCH₃.

The compounds include solvates and hydrates and pharmaceutically acceptable acid addition salts of the basic compounds of Formula I above.

The term pharmaceutically acceptable acid addition salt is intended to mean a relatively nontoxic acid addition salt either from inorganic or organic acids such as, for example, hydrochloric, hydrobromic, hydroiodic, sulfuric, phosphoric, acetic, citric, oxalic, malonic, salicyclic, malic, benzoic, gluconic, fumaric, succinic, ascorbic, maleic, tartaric, methanesulfonic and the like. The salts are prepared by contacting the free base form with a sufficient amount of the desired acid to produce a salt in the conventional manner. The free base forms may be regenerated by treating the salt form with a base.

The modified peptides of the present invention possess one or more chiral centers and each center may exist in the R(D) or S(L) configuration. The present invention includes all enantiomeric and epimeric forms as well as the appropriate mixtures thereof.

Some of the above novel peptides may be prepared in accordance with well-known procedures for preparing peptides from their constituent amino acids. Other of the novel peptides of the present invention are prepared by a step-wise procedure or by a fragment coupling procedure depending upon the particular final product desired.

A process for preparing a compound of formula I comprises:

(a) reacting an amino acid amide or ester of formula

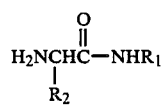

with a protected amino acid of formula

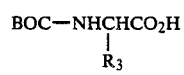

in an inert solvent to form the corresponding dipeptide of formula

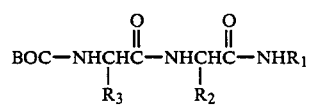

(b) removing from a compound of formula IV the protecting groups using an inorganic acid or an organic acid of comparable acidity to form the corresponding amine compound of formula

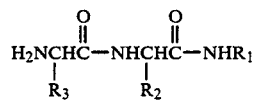

(c) condensing the resulting compound of formula V with a second protected amino acid compound of formula

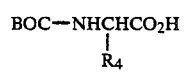

in an inert solvent to form the corresponding tripeptide of formula

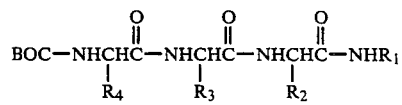

(d) repeating as desired steps (b) and (c) until the desired peptide is formed, and
(e) terminating, if desired, by acylating the amino group of step (b) with an acyl group.

The following scheme illustrates a process for the preparation of the compounds of the invention.

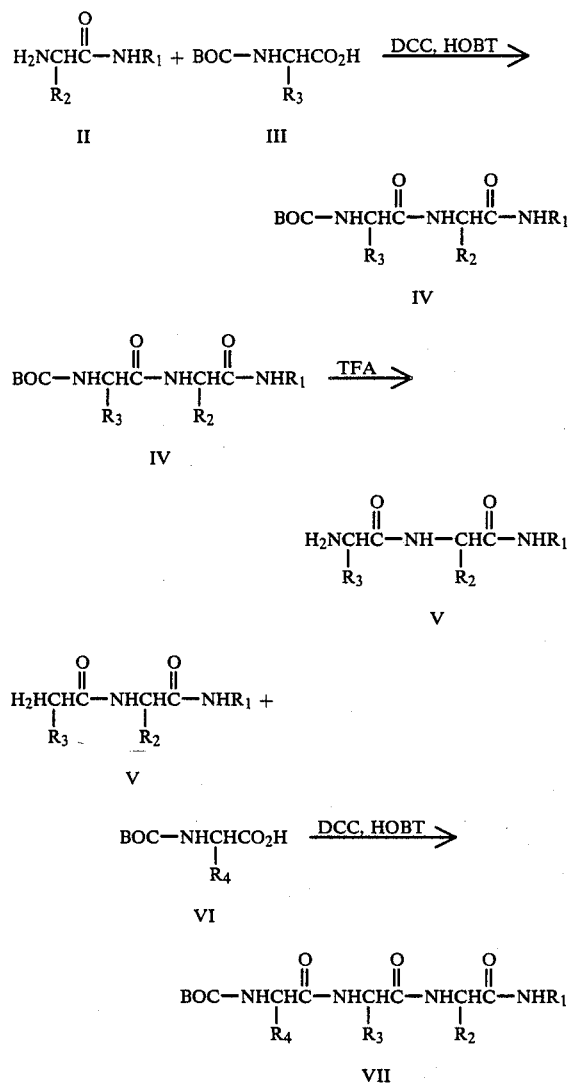

$R_1$–$R_4$ are typical side chains of amino acids.

According to this scheme, an amino acid amide (or ester) is condensed with a BOC (or Z)-protected amino acid in an inert solvent in the presence of DCC and HOBT. The BOC (or Z) protecting group of the product dipeptide is removed with TFA (hydrogen in the presence of palladium on carbon in the case of Z-protected peptides) and the resulting peptide with a free amino terminus is condensed with either BOC(or Z)-protected amino acids in the presence of DCC and HOBT. This process is repeated until the desired peptide is obtained. Optionally a terminal acyl group which is not readily removed may be added as a final step.

Inert solvents used in the condensation are $CH_2Cl_2$, DMF, THF, $CHCl_3$, dioxane, EtOAc, acetone, and the like. Preferred inert solvents include $CH_2Cl_2$, DMF, and THF.

The reaction temperature may vary between $-10°$ and $30°$ C. Preferably the temperature is between $0°$ and $25°$ C.

The reaction may run from two to forty hours. Preferably the reaction time is between four and sixteen hours.

THe BOC protecting group of the product dipeptide is removed with TFA in $CH_2Cl_2$ or $CHCl_3$, or with HCl gas in $CH_2Cl_2$. Preferably it is removed with TFA in $CH_2Cl_2$.

The Z protecting group may be removed with 30% HBr in HOAc or catalytically using palladium on carbon in $H_2O$, MeOH, EtOH, or HOAc. Preferably it is removed with palladium or carbon in MeOH.

The strategy of peptides chain assembly and selection and removal of protecting groups is discussed in Chapter 1, "The Peptide Bond," in "The Peptides. Analysis, Synthesis, Biology," E. Gross and J. Meienhofer, Eds., Academic Press, New York, NY, 1979, Vol. 1, p. 42–44.

The DCC/HOBT method of coupling is well known to those skilled in the art and is discussed in Chapter 5, "The Carbodiimide Method" by D. H. Rich and J. Singh in "The Peptides. Analysis, Synthesis, Biology," E. Gross and J. Meienhofer, Eds., Academic Press, New York, NY, 1979, Vol. 1, pp. 241–261.

Peptide coupling depends on activating the carboxyl group of the protected amino acid prior to condensing it with another peptide containing a free amino terminus. In addition to the DCC coupling method described above, other methods of activating the carboxyl group of a protected amino acid include:

(1) The azide method—described in Chapter 4 of the above reference.

(2) The mixed anhydride method—described in Chapter 6 of the above reference.

(3) The active ester method—described in Chapter 3 of the above reference.

The compounds of the present invention are useful for treating renin-associated hypertension and hyperaldosteronism. They are also useful as diagnostic tools in determining the presence of renin-associated hypertension.

Pharmaceutical compositions which comprise an effective amount of the compound in combination with a pharmaceutically acceptable carrier are part of the present invention. An important aspect of the present invention is a method of treating renin-associated hypertension in a mammal which comprises administering a pharmaceutical composition containing an effective amount of a compound of the invention in combination with a pharmaceutically acceptable carrier to the mammal.

Another equally important aspect of the present invention is a method of treating hyperaldosteronism in a mammal which comprises administering a pharmaceutical composition containing an effective amount of a compound of the invention in combination with a pharmaceutically acceptable carrier to the mammal.

The effectiveness of the aforementioned compounds is determined by a test for in vitro renin inhibitory activity. This activity is determined by a standard radioimmunoassay for angiotensin I. In this assay the enzyme, renin, incubated for two hours at 37° in the presence of a substrate, angiotensinogen, generates the product, angiotensin I. Test compounds are added to the incubation mixture. Relative activity is reported as the $IC_{50}$, which is the molar concentration of test compound causing a 50% inhibition of the renin activity.

TABLE II

| Example Number | Activity (IC$_{50}$) (M) |
| --- | --- |
| 1 | 1.2 × 10$^{-7}$ |
| 2 | 5.4 × 10$^{-7}$ |
| 3 | 1.2 × 10$^{-7}$ |
| 4 | 2.4 × 10$^{-7}$ |
| 5 | 1.4 × 10$^{-6}$ |
| 6 | 3.5 × 10$^{-7}$ |
| 7 | 2.3 × 10$^{-5}$ |
| 8 | 1.1 × 10$^{-6}$ |

As can be seen from the above table, the compounds of the present invention have a significant effect on the activity of renin and thus are useful for the treatment of hypertension and hyperaldosteronism.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders or tablet disintegrating agents; it can also be encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 to 10 to about 70 percent of the active ingredient. Suitable solid carriers are magnesium carbonate, magnesium stearate, talc, sugar, lactose, pectin, dextrin, starch, gelatin, tragacanth, methylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredient is dispersed homogeneously therein by stirring. The molten homogeneous mixture is then poured into convenient sized molds, allowed to cool, and thereby solidify.

Liquid form preparations include solutions, suspensions, and emulsions. As an example may be mentioned water or water/propylene glycol solutions for parenteral injection. Liquid preparations can also be formulated in solution in aqueous polyethyleneglycol solution. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like, as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tables, capsules, and powders in vials or ampules. The unit dosage form can also be a capsule, cachet, or tablet itself, or it can be the appropriate number of any of these in packaged form.

The quantity of active compound in a unit dose of preparation may be varied or adjusted from 1 mg to 500 mg, preferably 5 to 100 mg according to the particular application and the potency of the active ingredient. The compositions can, if desired, also contain other compatible therapeutic agents.

In therapeutic use as renin inhibitors, the mammalian dosage range for a 70 kg subject is from 1 to 1500 mg of body weight per day or preferably 25 to 750 mg of body weight per day optionally in divided portions. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

The following examples are provided to enable one skilled in the art to practice the present invention. These examples are not intended in any way to limit the scope of the invention but are illustrative thereof.

EXAMPLE 1

BOC-PHE-LEU-STA-MET-PRO-NHCH$_2$Ph

To a solution of 0.5 g (0.71 mmole) of BOC-LEU-STA-MET-PRO-NHCH$_2$Ph in CH$_2$Cl$_2$ was added an equal volume of TFA. The reaction mixture was stirred at room temperature for 40 minutes. It was then concentrated, CH$_2$Cl$_2$ added, and then concentrated again. This step was repeated. CH$_2$Cl$_2$ was then added and the solution was cooled in an ice bath.

In a separate flask 0.19 g (0.71 mmole) of BOC-PHE was dissolved in DMF/CH$_2$Cl$_2$. To this was added 0.11 g (0.71 mmole) of hydroxybenzotriazole and 0.16 g (0.8 mmole) of dicyclohexylcarbodiimide.

The cooled LEU-STA-MET-PRO-NHCH$_2$Ph.TFA solution was made basic with Et$_3$N and was then added to the above BOC-PHE solution. The reaction was stirred at room temperature for three days and the CH$_2$Cl$_2$ then removed under reduced pressure. The residual mixture in DMF was filtered and EtOAc added to the filtrate. The organic solution was washed with citric acid solution, Na$_2$CO$_3$ and then brine. After drying over MgSO$_4$ the solvent was removed under reduced pressure to give the crude product which was purified by chromatography on silica gel.

Calcd. for C$_{45}$H$_{68}$N$_6$O$_8$S: C, 63.35; H, 8.03; N, 9.85 Found C, 63.05; H, 8.01; N, 9.73.

EXAMPLE 2

BOC-PHE-LEU-STA-MET(O)-PRO-NHCH$_2$Ph

To a solution of 0.14 g (0.16 mmole) of BOC-PHE-LEU-STA-MET-PRO-NHCH$_2$Ph in MeOH was added 10 ml (0.45 mmole) of 0.5N NaIO$_4$ solution. The reaction mixture was stirred for one hour and then concentrated under reduced pressure. The product was extracted into EtOAc and washed with NaHSO$_3$. The organic solvent was removed under reduced pressure to give the product.

Calcd. for C$_{45}$H$_{68}$N$_6$O$_9$S.H$_2$O: C, 60.92; H, 7.95; N, 9.47 Found C, 60.59; H, 7.70; N, 9.25.

EXAMPLE 3

DNMA-LEU-STA-MET-PRO-NHCH$_2$Ph

To a solution of 0.5 g (0.71 mmole) of BOC-LEU-STA-MET-PRO-NHCH$_2$Ph in CH$_2$Cl$_2$ was added an equal volume of TFA. The reaction mixture was stirred at room temperature for 0.5 hours and then was concentrated under reduced pressure. CH$_2$Cl$_2$ was added and the solution again concentrated. The residue was taken up in CH$_2$Cl$_2$, cooled in an ice bath, and Et$_3$N added until the solution was basic.

In a separate flask a solution of 0.11 g (0.71 mmole) of hydroxybenzotriazole and 0.24 g (0.71 mmole) of di-(α-naphthylmethyl)acetic acid in DMF/CH$_2$Cl$_2$ was prepared.

The two solutions were combined and 0.15 g (0.71 mmole) of dicyclohexylcarbodiimide was added. The reaction mixture was stirred at room temperature overnight, filtered, and concentrated under reduced pressure. The residue was dissolved in EtOAc and washed with citric acid solution, Na$_2$CO$_3$ solution, and brine. After drying over MgSO$_4$, the solvent was removed under reduced pressure to give 0.6 g of the product as a white foam.

Calcd. for C$_{55}$H$_{69}$N$_5$O$_6$S: C, 71.17; H, 7.49; N, 7.54 Found C, 71.28; H, 7.50; N, 7.80.

EXAMPLE 4

DNMA-LEU-STA-MET(O)-PRO-NHCH$_2$Ph

To a solution of 0.14 g (0.15 mmole) DNMA-LEU-STA-MET-PRO-NHCH$_2$Ph in MeOH was added 10 ml (0.45 mmole) of 0.5N NaIO$_4$ solution. The reaction was stirred at room temperature for one hour and then filtered. The filtrate was concentrated under reduced pressure and the residue was taken up in EtOAc. This solution was washed with NaHSO$_3$ solution and dried with MgSO$_4$. After removal of the drying agent by filtration, the filtrate was concentrated under reduced pressure to give the product.

Calcd. for C$_{55}$H$_{69}$N$_5$O$_7$S.H$_2$O: C, 68.65; H, 7.44; N, 7.28 Found C, 68.14; H, 7.48; N, 7.66.

EXAMPLE 5

BOC-PHE-LEU-STA-PRO-NHCH$_2$Ph

To a solution of 1.3 g (2.3 mmole) of BOC-LEU-STA-PRO-NHCH$_2$Ph in CH$_2$Cl$_2$ was added an equal volume of TFA. The reaction mixture was stirred at room temperature for 0.5 hours and then concentrated under reduced pressure. CH$_2$Cl$_2$ was added and the solution again concentrated. This process was repeated. The residue was dissolved in CH$_2$Cl$_2$, cooled in ice, and made basic with Et$_3$N.

In a separate flask a solution of 0.61 g (2.3 mmole) of BOC-PHE and 0.35 g (2.3 mmole) of hydroxybenzotriazole in DMF/CH$_2$Cl$_2$ was prepared.

The two solutions were combined and 0.55 g (2.7 mmole) of dicyclohexylcarbodiimide was added. The reaction mixture was stirred at room temperature overnight, filtered, and concentrated under reduced pressure. The residue was taken up in EtOAc and washed with citric acid solution, Na$_2$CO$_3$ solution and brine. The organic phase was dried, concentrated under reduced pressure, and the residue chromatographed on silica gel to yield the product.

Calcd. for C$_{40}$H$_{59}$N$_5$O$_7$.0.25CHCl$_3$: C, 64.30; H, 7.94; N, 9.32 Found C, 64.47; H, 7.66; N, 9.57.

EXAMPLE 6

BOC-PHE-LEU-STA-GLU(OCH$_2$Ph)-PRO-OCH$_3$

To a solution of 1.5 g (2.1 mmole) of BOC-LEU-STA-GLU(OCH$_2$Ph)-PRO-OCH$_3$ in CHCl$_2$ was added an equal volume of TFA. The reaction was stirred at room temperature for one-half hour and then concentrated. CH$_2$Cl$_2$ was added and the solution again concentrated. This process was repeated. The residue was dissolved in CH$_2$Cl$_2$ and cooled in an ice bath. In a separate flask, to a solution of 0.56 g (2.1 mmole) of BOC-PHE in DMF/CH$_2$Cl$_2$ was added 0.32 g (2.1 mmole) of hydroxybenzotriazole. The cooled solution of the LEU-STA-GLU(OCH$_2$Ph)-PRO-OME.TFA was made basic with ET$_3$N and added to the BOC-PHE solution followed by 0.43 g (2.1 mmole) of dicyclohexylcarbodiimide. The reaction was stirred at room temperature overnight, filtered, and concentrated. The residue was taken up in EtOAc and washed with citric acid solution, Na$_2$CO$_3$ solution, and brine. The organic phase was dried and concentrated. The product solidified when treated with petroleum ether/ether.

Calcd. for C$_{46}$H$_{67}$N$_5$O$_{11}$: C, 63.80; H, 7.80; N, 8.08 Found C, 64.24; H, 7.74; N, 8.26.

EXAMPLE 7

BOC-PHE-GLY-STA-GLU(OCH$_2$Ph)-PRO-OCH$_3$

To a solution of 0.5 g (0.75 mmole) of BOC-GLY-STA-GLU(OCH$_2$Ph)-PRO-OCH$_3$ in CH$_2$Cl$_2$ was added an equal volume of TFA. The reaction was stirred at room temperature for one-half hour and then concentrated. CH$_2$Cl$_2$ was added and the solution again concentrated. This process was repeated. The residue was dissolved in CH$_2$Cl$_2$ and cooled in an ice bath. In a separate flask, to a solution of 0.2 g (0.75 mmole) of BOC-PHE in DMF/CH$_2$Cl$_2$ was added 0.11 g (0.75 mmole) of hydroxybenzotriazole. The cooled solution of the GLY-STA-GLU(OCH$_2$Ph)-PRO-OCH$_3$.TFA was made basic with Et$_3$N and added to the BOC-PHE solution followed by 0.15 g (0.75 mmole) of dicyclohexylcarbodiimide. The reaction was stirred at room temperature for three days, filtered, and concentrated. The residue was taken up in EtOAc and washed with citric acid solution, Na$_2$CO$_3$ solution, and brine. The organic phase was dried, concentrated, and chromatographed on silica gel to give the product.

Calcd. for C$_{42}$H$_{59}$N$_5$O$_{11}$.0.5H$_2$O: C, 61.60; H, 7.38; N, 8.55 Found C, 61.35; H, 7.37; N, 8.60.

EXAMPLE 8

BOC-PHE-LEU-STA-GLN-PRO-OCH$_3$

To a solution of 0.74 g (1.2 mmole) of BOC-LEU-STA-GLN-PRO-OCH$_3$ in CH$_2$Cl$_2$ was added an equal volume of TFA. The reaction was stirred at room temperature for one-half hour and then concentrated. CH$_2$Cl$_2$ was added and the solution again concentrated. This process was repeated. The residue was dissolved in CH$_2$Cl$_2$ and cooled in an ice bath. In a separate flask, to a solution of 0.32 g (1.2 mmole) of BOC-PHE in DMF/CH$_2$Cl$_2$ was added 0.18 g (1.2 mmole) of hydroxybenzotriazole. The cooled solution of the LEU-STA-GLN-PRO-OCH$_3$.TFA was made basic with Et$_3$N and added to the BOC-PHE solution followed by 0.27 g (1.3 mmole) of dicyclohexylcarbodiimide. The reaction was stirred at room temperature overnight, filtered, and concentrated. The residue was taken up in EtOAc and washed with citric acid solution, Na$_2$CO$_3$ solution, and brine. The organic phase was dried, concentrated, taken up again in EtOAc, and filtered. Petroleum ether was added to the filtrate precipitating the product as a white solid.

Calcd. for C$_{39}$H$_{62}$N$_{56}$O$_{10}$.0.5H$_2$O: C, 59.75; H, 8.10; N, 10.72 Found C, 59.97; H, 8.14; N, 10.65.

INTERMEDIATES FOR EXAMPLES 1 AND 3

BOC-PRO-NHCH$_2$Ph

To a solution of 15.0 g (0.07 mole) of BOC-PRO in DMF/CH$_2$Cl$_2$ was added 10.7 g (0.07 mole) of hydroxybenzotriazole, 7.5 g (0.07 mole) of benzylamine, and 15.9 g (0.077 mole) of dicyclohexylcarbodiimide. The reaction mixture was stirred at room temperature overnight. The CH$_2$Cl$_2$ was removed under reduced pressure and the residual DMF mixture was filtered and the collected solid was washed on the filter with EtOAc. The combined EtOAc and DMF solution was washed with citric acid solution, Na$_2$CO$_3$ solution, and brine. After drying over MgSO$_4$, the MgSO$_4$ was filtered off and washed with hot EtOAc. Cooling gave 17.4 g of product.

Calcd. for C$_{17}$H$_{24}$N$_2$O$_3$: C, 67.08; H, 7.95; N, 9.20 Found C, 67.01; H, 7.99; N, 9.50.

BOC-MET-PRO-NHCH$_2$Ph

To a solution of 2.3 g (7.5 mmole) of BOC-PRO-NHCH$_2$Ph in CH$_2$Cl$_2$ was added an equal volume of TFA. After stirring at room temperature for 0.5 hours, the solution was concentrated under reduced pressure, CH$_2$Cl$_2$ added, and the solution again concentrated. This process was repeated. The residue was then dissolved in CH$_2$Cl$_2$, cooled in an ice bath, and made basic with Et$_3$N.

In a separate flask was prepared a solution of 1.8 g (7.5 mmole) of BOC-MET, 1.15 g (7.5 mmole) of hydroxybenzotriazole, and 1.7 g (8.3 mmole) of dicyclohexylcarbodiimide in DMF/CH$_2$Cl$_2$.

The two solutions are mixed and allowed to stir at room temperature overnight. The CH$_2$Cl$_2$ was removed under reduced pressure and the residual DMF mixture filtered. The filtrate was diluted with EtOAc and washed with citric acid solution, Na$_2$CO$_3$ solution, and then brine. After drying over MgSO$_4$, the solvent was removed under reduced pressure to give the crude product. Chromatography on silica gel, eluting with CHCl$_3$, gave 2.0 of product.

Calcd. for C$_{32}$H$_{33}$N$_3$O$_4$S.0.2CHCl$_3$: C, 58.03; H, 7.29; N, 9.14 Found C, 57.75; H, 7.56; N, 9.42.

BOC-STA-MET-PRO-NHCH$_2$Ph

To a solution of 1.9 g (4.6 mmole) of BOC-MET-PRO-NHCH$_2$Ph in CH$_2$Cl$_2$ was added an equal volume of TFA. After stirring at room temperature for 45 minutes, the solution was concentrated under reduced pressure, CH$_2$Cl$_2$ added, and the solution again concentrated. This process was then repeated. The residue was taken up in CH$_2$Cl$_2$, cooled in an ice bath, and made basic with Et$_3$N.

In a separate flask was prepared a solution of 1.26 g (4.6 mmole) of BOC-STA, 0.7 g (4.6 mmole) of hydroxybenzotriazole, and 1.05 g (5.1 mmole) of dicyclohexylcarbodiimide in DMF/CH$_2$Cl$_2$.

The two solutions were mixed and allowed to stir at room temperature for three days. The CH$_2$Cl$_2$ was removed under reduced pressure and the residual DMF mixture filtered. The filtrate was diluted with EtOAc and washed with citric acid solution, Na$_2$CO$_3$ solution, and then brine. After drying over MgSO$_4$ and removal of the solvent under reduced pressure, the crude product was chromatographed on silica gel to give 1.6 g of product.

Calcd. for C$_{30}$H$_{48}$N$_4$O$_6$S: C, 60.79; H, 8.16; N, 9.45 Found C, 60.60; H, 8.04; N, 9.64.

BOC-LEU-STA-MET-PRO-NHCH$_2$Ph

To a solution of 1.5 g (2.5 mmole) of BOC-STA-MET-PRO-NHCH$_2$Ph in CH$_2$Cl$_2$ was added an equal volume of TFA. After stirring at room temperature for 0.5 hours, the solution was concentrated under reduced pressure, CH$_2$Cl$_2$ added, and the solution again concentrated. This process was then repeated. The residue was taken up in CH$_2$Cl$_2$, cooled in an ice bath, and made basic with Et$_3$N.

In a separate flask was prepared a solution of 0.38 g (2.5 mmole) of hydroxybenzotriazole, 0.62 g (2.5 mmole) of BOC-LEU.H$_2$O, and 0.58 g (2.8 mmole) of dicyclohexylcarbodiimide in CH$_2$Cl$_2$/DMF.

The two solutions were mixed and allowed to stir at room temperature overnight. The mixture was concentrated under reduced pressure, diluted with EtOAc, and filtered. The filtrate was washed with citric acid solution, Na$_2$CO$_3$ solution, and then brine. After drying over MgSO$_4$ and removal of the solvent under reduced pressure, the crude product was chromatographed on silica gel to give 1.0 g of product.

Calcd. for C$_{36}$H$_{59}$N$_5$O$_7$S: C, 61.25; H, 8.42; N, 9.92 Found C, 61.17; H, 8.20; N, 9.83.

INTERMEDIATES FOR EXAMPLE 5

BOC-STA-PRO-NHCH$_2$Ph

To a solution of 3.0 g (0.01 mole) of BOC-PRO-NHCH$_2$Ph in CH$_2$Cl$_2$ was added an equal volume of TFA. The reaction was stirred at room temperature for 0.75 hours and then concentrated. CH$_2$Cl$_2$ was added and the solution again concentrated. This process was repeated. The residue was dissolved in CH₂Cl₂ and cooled in an ice bath. In a separate flask, to a solution of 2.8 g (0.01 mole) of BOC-STA in DMF/CH₂Cl₂ was added 1.5 g (0.01 mole) of hydroxybenzotriazole. The cooled solution of the PRO-NHCH₂Ph.TFA was maded basic with Et₃N and added to the BOC-STA solution followed by 2.3 g (0.01 mole) of dicyclohexylcarbodiimide. The reaction was stirred at room temperature for three days, filtered and concentrated. The residue was taken up in EtOAc and washed with citric acid solution, Na₂CO₃ solution, and brine. The organic phase was dried, concentrated, and the residue chromatographed on silica gel to yield the product.

Calcd. for $C_{25}H_{39}N_3O_5 \cdot 0.05CHCl_3$: C, 64.35; H, 8.42; N, 8.99 Found C, 64.36; H, 8.50; N, 8.88.

BOC-LEU-STA-PRO-NHCH₂Ph

To a solution of 1.5 g (3.2 mmole) of BOC-STA-PRO-NHCH₂Ph in CH₂Cl₂ was added an equal volume of TFA. The reaction was stirred at room temperature for one-half hour and then concentrated. CH₂Cl₂ was added and the solution again concentrated. This process was repeated. The residue was dissolved in CH₂Cl₂ and cooled in an ice bath. In a separate flask, to a solution of 0.8 g (3.2 mmole) of BOC-LEU.H₂O in DMF/CH₂Cl₂ was added 0.5 g (3.2 mmole) of hydroxybenzotriazole. The cooled solution of the STA-PRO-NHCH₂Ph.TFA was made basic with Et₃N and added to the BOC-LEU solution followed by 0.72 g (3.5 mmole) of dicyclohexylcarbodiimide. The reaction was stirred at room temperature overnight, filtered, and concentrated. The residue was taken up in EtOAc and washed with citric acid solution, Na₂CO₃ solution, and brine. The organic phase was dried, concentrated, and the residue chromatographed on silica gel to yield the product.

Calcd. for $C_{31}H_{50}N_4O_6 \cdot 0.1CHCl_3$: C, 63.67; H, 8.61; N, 9.55 Found C, 63.90; H, 8.42; N, 9.64.

INTERMEDIATES FOR EXAMPLE 6

BOC-GLU(OCH₂Ph)-PRO-OCH₃

To a solution of 9.1 g (0.027 mole) of BOC-GLU(OCH₂Ph) in DMF/CH₂Cl₂ was added 4.1 g (0.027 mole) of hydroxybenzotriazole. In a separate flask 3.8 ml (0.028 mole) of Et₃N was added to a cooled mixture of 4.5 g (0.027 mole) of PRO-OME.HCl in CH₂Cl₂. This was then added to the above solution followed by 6.2 g (0.03 mole) of dicyclohexylcarbodiimide. The reaction was stirred at room temperature, filtered, and concentrated. The residue was dissolved in EtOAc and washed with citric acid solution, Na₂CO₃ solution, and brine. After concentration of the organic phase the residue was chromatographed on silica gel with CHCl₃ to give 3.75 g of product.

Calcd. for $C_{23}H_{32}N_2O_7 \cdot 0.4CHCl_3$: C, 56.63; H, 6.58; N, 5.64 Found, C, 56.51; H, 6.36; N, 5.90.

BOC-STA-GLU(OCH₂Ph)-PRO-OCH₃

To a solution of 3.5 g (7.8 mmole) of BOC-GLU(OCH₂Ph)-PRO-OCH₃ in CH₂Cl₂ was added an equal volume of TFA. The reaction was stirred at room temperature for one-half hour and then concentrated. CH₂Cl₂ was added and the solution again concentrated. This process was repeated. The residue was dissolved in CH₂Cl₂ and cooled in an ice bath. In a separate flask, to a solution of 2.1 g (7.8 mmole) of BOC-STA in DMF/CH₂Cl₂ was added 1.2 g (7.8 mmole) of hydroxybenzotriazole. The cooled solution of the GLU-(OCH₂Ph)-PRO-OCH₃.TFA was made basic with Et₃N and added to the BOC-STA solution followed by 1.8 g (8.6 mmole) of dicyclohexylcarbodiimide. The reaction was stirred at room temperature for three days, filtered, and concentrated. The residue was taken up in EtOAc and washed with citric acid solution, Na₂CO₃ solution, and brine. The organic phase was dried, concentrated, and then chromatographed on silica gel with CHCl₃ to give the product.

Calcd. for $C_{31}H_{47}N_3O_9 \cdot 0.1CHCl_3$: C, 60.48; H, 7.69; N, 6.80 Found C, 60.47; H, 7.83; N, 7.06.

BOC-LEU-STA-GLU(OCH₂Ph)-PRO-OCH₃

To a solution of 2.0 g (3.3 mmole) of BOC-STA-GLU(OCH₂Ph)-PRO-OCH₃ in CH₂Cl₂ was added an equal volume of TFA. The reaction was stirred at room temperature for one-half hour and then concentrated. CH₂Cl₂ was added and the solution again concentrated. This process was repeated. The residue was dissolved in CH₂Cl₂ and cooled in an ice bath. In a separate flask, to a solution of 0.82 g (3.3 mmole) of BOC-LEU.H₂O in DMF/CH₂Cl₂ was added 0.5 g (3.3 mmole) of hydroxybenzotriazole. The cooled solution of STA-GLU(OCH₂Ph)-PRO-OCH₃.TFA was made basic with Et₃N and added to the BOC-LEU solution followed by 0.68 g (3.3 mmole) of dicyclohexylcarbodiimide. The reaction was stirred at room temperature overnight, filtered, and concentrated. The residue was taken up in EtOAc and washed with citric acid solution, Na₂CO₃ solution, and brine. The organic phase was dried, concentrated, and then chromatographed on silica gel with CHCl₃ to give the product.

Calcd. for $C_{37}H_{58}N_4O_{10} \cdot 0.25CHCl_3$: C, 59.75; H, 7.84; N, 7.48 Found C, 60.16; H, 7.53; N, 7.79.

INTERMEDIATE FOR EXAMPLE 7

BOC-GLY-STA-GLU(OCH₂Ph)-PRO-OCH₃

To a solution of 1.1 g (1.8 mmole) of BOC-STA-GLU(OCH₂Ph)-PRO-OCH₃ in CH₂Cl₂ was added an equal volume of TFA. The reaction was stirred at room temperature for one-half hour and then concentrated. CH₂Cl₂ was added and the solution again concentrated. This process was repeated. The residue was dissolved in CH₂Cl₂ and cooled in an ice bath. In a separate flask, to a solution of 0.28 g (1.8 mmole) of BOC-GLY in DMF/CH₂Cl₂ was added 0.28 g (1.8 mmole) of hydroxybenzotriazole. The cooled solution of the STA-GLU(OCH₂Ph)-PRO-OCH₃.TFA was made basic with Et₃N and added to the BOC-GLY solution followed by 0.41 g (2.0 mmole) of dicyclohexylcarbodiimide. The reaction was stirred at room temperature overnight, filtered, and concentrated. The residue was taken up in EtOAc and washed with citric acid solution, Na₂CO₃ solution, and brine. The organic phase was dried, concentrated, and chromatographed on silica gel to give the 0.7 g of product.

Calcd. for $C_{33}H_{50}N_4O_{10} \cdot 1.1CHCl_3$: C, 51.57; H, 6.49; N, 7.06 Found C, 51.44; H, 6.48; N, 7.48.

INTERMEDIATES FOR EXAMPLE 8

BOC-GLN-PRO-OCH₃

To a cooled mixture of 4.5 g (0.027 mole) of PRO-OCH₃.HCl in DMF was added 3.8 ml (0.027 mole) of Et₃N. This was then added to a solution of 9.9 g (0.027 mole) of the para-nitrophenyl ester of BOC-GLN in DMF. The reaction mixture was stirred at room temperature overnight and then concentrated under reduced pressure. The residue was taken up in EtOAc and washed with citric acid solution, Na₂CO₃ solution (five times), and then with brine. The citric acid wash was re-extracted with EtOAc. The combined EtOAc solutions were dried over MgSO₄ and concentrated under reduced pressure to give the product.

BOC-STA-GLN-PRO-OCH₃

To a solution of 5.0 g (0.014 mole) of BOC-GLN-PRO-OCH₃ in CH₂Cl₂ was added an equal volume of TFA. The reaction was stirred at room temperature for one-half hour and then concentrated. CH₂Cl₂ was added and the solution again concentrated. This process was repeated. The residue was dissolved in CH₂Cl₂ and cooled in an ice bath. In a separate flask, to a solution of 3.9 g (0.014 mole) of BOC-STA in DMF/CH₂Cl₂ was added 2.1 g (0.014 mole) of hydroxybenzotriazole. The cooled solution of the GLN-PRO-OCH₃.TFA was made basic with Et₃N and added to the BOC-STA solution followed by 3.1 g (0.015 mole) of dicyclohexylcarbodiimide. The reaction was stirred at room temperature overnight, filtered, and concentrated. The residue was taken up in EtOAc and washed with citric acid solution, Na₂CO₃ solution, and brine. The citric acid wash was re-extracted with EtOAc. The combined EtOAc solutions were dried over MgSO₄ and concentrated under reduced pressure. The residue was chromatographed on silica gel to give the product.

BOC-LEU-STA-GLN-PRO-OCH₃

To a solution of 0.9 g (1.7 mmole) of BOC-STA-GLN-PRO-OCH₃ in CH₂Cl₂ was added an equal volume of TFA. The reaction was stirred at room temperature for one-half hour and then concentrated. CH₂Cl₂ was added and the solution again concentrated. This process was repeated. The residue was dissolved in CH₂Cl₂ and cooled in an ice bath. In a separate flask, to a solution of 0.42 g (1.7 mmole) of BOC-LEU.H₂O in DMF/CH₂Cl₂ was added 0.26 g (1.7 mmole) of hydroxybenzotriazole. The cooled solution of the STA-GLN-PRO-OCH₃.TFA was made basic with Et₃N and added to the BOC-LEU solution followed by 0.39 g (1.9 mmole) of dicyclohexylcarbodiimide. The reaction was stirred at room temperature overnight, filtered, and concentrated. The residue was taken up in EtOAc and washed with citric acid solution, Na₂CO₃ solution, and brine. The organic phase was dried, concentrated, taken up again in EtOAc, and filtered. Removal of the solvent under reduced pressure gave the product.

We claim:

1. A peptide of the formula

    ACYL—X—Y—T—U—V—W    I or a pharmaceutically acceptable salt thereof, wherein
ACYL is BOC, IBU, IVA, NVA, Z, or DNMA;
X is absent, PHE, HOMOPHE, NAPHTHYLALA, TRP, CYCLOHEXYLALA, (Me⁵)PHE, VAL, ILE or LEU, with the proviso that when X is absent ACYL is DNMA;
Y is CYS, SMeCYS, SOMeCYS, SO₂MeCYS, ASP, ASP(OCH₃), ASP(OC₂H₅), ASP(OCH₂Ph), ASP-(O-t-Bu), ASN, SER, SER(CH₂Ph), SER(CH₃), SER(C₂H₅), LEU, GLY, ILE, VAL, NLE, HIS, PHE, ARG, ARG(NO₂), ALA, ORN, ORN(Z), ORN(BOC), ORN(PHT), ORN(Ac), LYS, LYS(Z), LYS(BOC), LYS(PHT), LYS(Ac), GLN, GLU, GLU(OCH₂Ph), GLU(O-t-Bu), GLU(OCH₃), GLU(OC₂H₅), MET, MET(O), MET(O)₂,

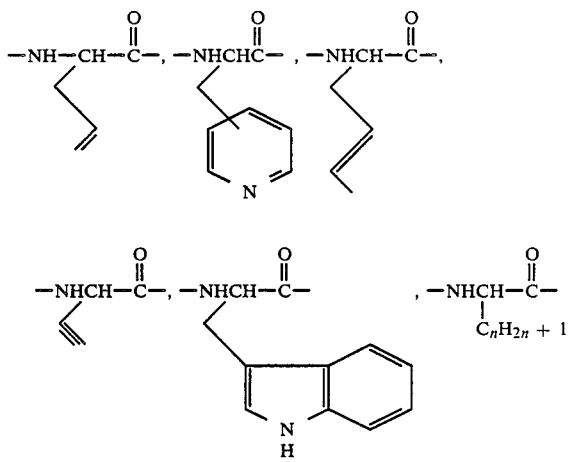

wherein n is an integer of 2, or 4–10,

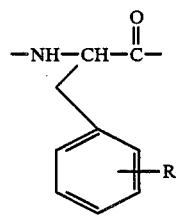

wherein R is alkyl, halogen or alkoxy,

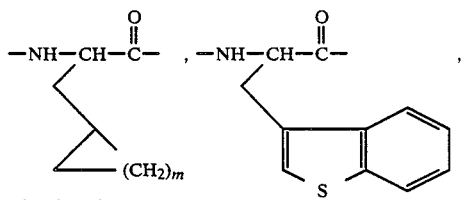

wherein m is an integer of from 1 to 3

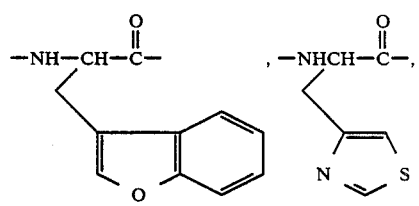

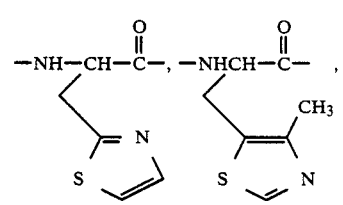

-continued

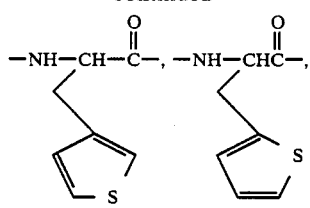

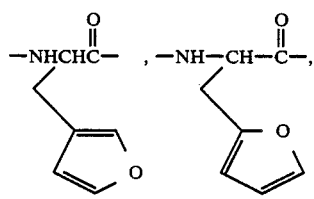

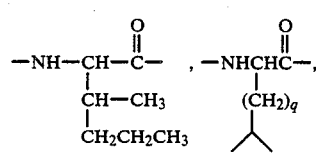

wherein q is an integer of from 2 to 4,

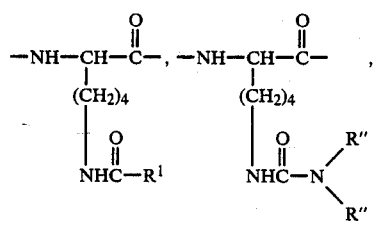

where $R^1$ is an alkyl group of from 1–4 carbon atoms,

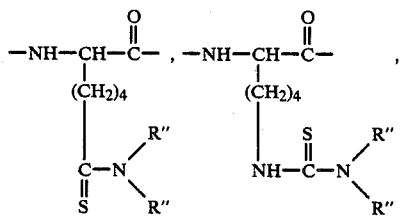

wherein R'' is H or an alkyl of from 1 to 4 carbon atoms;

T is STA, PHSTA, or CYSTA;

U is, GLU, GLU(OCH₂Ph), GLU(OCH₃), GLN, MET, MET(O), SMeCYS, GLU(OC₂H₅), GLU(O-t-Bu), SOMeCYS, ASP, ASP(OCH₂Ph), ASP(OCH₃), ASP(OC₂H₅),

ASN, 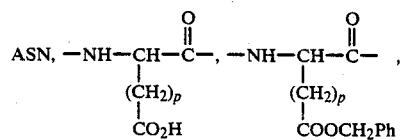

-continued

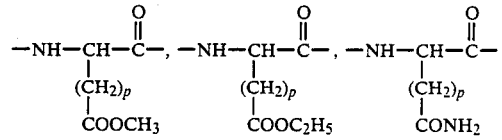

wherein p is the integer 3 or 4;

V is PRO, HYDROXYPRO, piperidine-2-carboxylic acid,

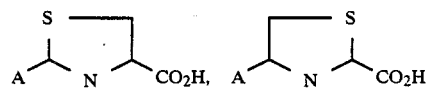

wherein A is an alkyl of from one to four carbon atoms, aralkyl, or aryl wherein aryl is unsubstituted phenyl or phenyl substituted with a lower alkyl or halogen, and W is

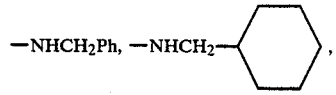

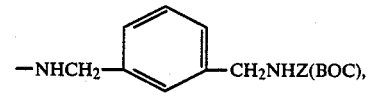

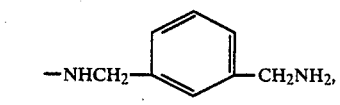

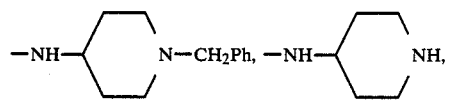

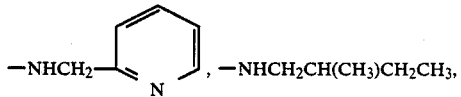

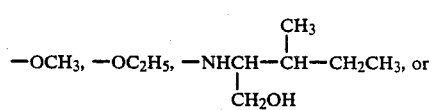

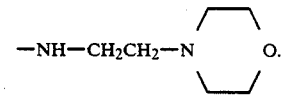

2. A peptide according to claim 1 wherein
ACYL is BOC, IBU, IVA, NVA, Z, or DNMA;
X is absent, PHE, HOMOPHE, NAPHTHYLALA, TRP, or CYCLOHEXYLALA; with the proviso that when X is absent, ACYL is DNMA;
Y is LEU, GLY, ILE, VAL, NLE, HIS, PHE, ARG, or ARG(NO₂);
T is STA, PHSTA, or CYSTA;
U is absent, GLU, GLU(OCH₂Ph), GLU(OCH₃), MET(O)₂, GLN, MET, MET(O), SMeCYS, GLU(OC₂H₅), or SOMeCYS;

V is PRO; and
W is

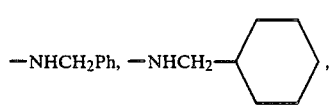

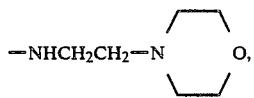

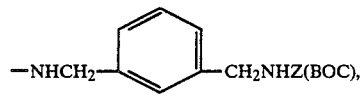

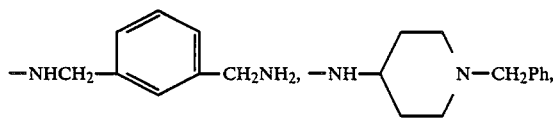

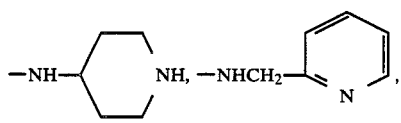

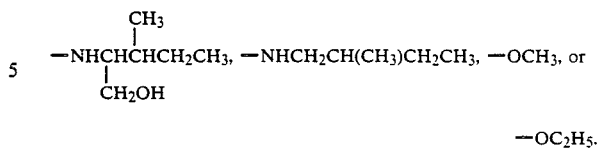

—OC₂H₅.

3. A peptide according to claim 1 wherein the peptide is a member selected from the group consisting of
BOC-PHE-LEU-STA-MET-PRO-NHCH₂Ph,
BOC-PHE-LEU-STA-MET(O)-PRO-NHCH₂Ph,
DNMA-LEU-STA-MET-PRO-NHCH₂Ph,
DNMA-LEU-STA-MET(O)-PRO-NHCH₂Ph,
BOC-PHE-LEU-STA-PRO-NHCH₂Ph,
BOC-PHE-LEU-STA-GLU(OCH₂Ph)-PRO-OCH₃
BOC-PHE-GLY-STA-GLU(OCH₂Ph)-PRO-OCH₃, and
BOC-PHE-LEU-STA-GLN-PRO-OCH₃.

4. A pharmaceutical composition comprising a renin-inhibitory effective amount of a compound as claimed in claim 1 together with a pharmaceutically acceptable carrier.

5. A method of treating renin-associated hypertension which comprises administering to a mammal a pharmaceutical composition as claimed in claim 4.

* * * * *